US005641677A

United States Patent [19]
Ochoa et al.

[11] Patent Number: 5,641,677
[45] Date of Patent: Jun. 24, 1997

[54] METHOD OF ENHANCING THE IMMUNOTHERAPEUTIC ACTIVITY OF IMMUNE CELLS BY DEPLETION OF CD8+ T CELLS

[75] Inventors: Augusto Carlos Ochoa, Washington, D.C.; Robin Lee Geller, Edina; Fritz H. Bach, Minneapolis, both of Minn.

[73] Assignee: Regents of the University of Minnesota, Minneapolis, Minn.

[21] Appl. No.: 288,428

[22] Filed: Aug. 10, 1994

Related U.S. Application Data

[63] Continuation of Ser. No. 960,297, Oct. 13, 1992, abandoned, which is a continuation of Ser. No. 681,074, Apr. 5, 1991, abandoned.

[51] Int. Cl.$^6$ ........................................... C12N 5/06
[52] U.S. Cl. ........................ 435/240.21; 435/240.2; 435/240.1; 435/240.25; 424/93.71
[58] Field of Search .................... 424/130.1, 144.1, 424/93.71; 435/240.2, 240.25, 240.1

[56] References Cited

U.S. PATENT DOCUMENTS

| | | |
|---|---|---|
| 4,690,915 | 9/1987 | Rosenberg . |
| 4,808,151 | 2/1989 | Dunn et al. . |

FOREIGN PATENT DOCUMENTS

| | | |
|---|---|---|
| 0405972 | 1/1991 | European Pat. Off. . |
| 0409655 | 1/1991 | European Pat. Off. . |
| WO88/00970 | 2/1988 | WIPO . |
| WO89/05657 | 6/1989 | WIPO . |
| WO89/09831 | 10/1989 | WIPO . |
| WO90/04633 | 5/1990 | WIPO . |

OTHER PUBLICATIONS

Tsoukas et al., "Activation of Resting T Lymphocytes By Anti–CD3 (T3) Antibodies in the Absence of Monocytes", The Journal of Immunology, vol. 135, No. 3, Sep. 1985, pp. 1719–1723.

Hogan et al., "Lymphokine–Activated and Natural Killer Cell Activity in Human Intestinal Mucosa", The Journal of Immunology, vol. 135, No. 3, Sep. 1985, pp. 1731–1738.

P.M. Anderson et al., Cancer Immunol. Immunother., 1988, 27, 82, "Augmentation of cell number and LAK activity in peripheral blood mononuclear cells activated with anti–CD3 and interleukin–2".

P.M. Anderson et al., J. Immunol., 1989, 142, 1383, "Anti–CD3+ IL–2–Stimulated Murine Killer Cells in Vitro Generation and In Vivo Antitumor Activity".

L.S. Davis et al., Cell Immunol., 1989, 118, 208, "T Cell Activation Induced by Anti–CD3 Antibodies Requires Prolonged Stimulation of Protein Kinase C".

Dianzani et al., Eur. J. Immunol., 19: 1037 (1989), "CD8+ CD11b+ peripheral blood T lymphocytes contain lymphokine–activated killer cell precursors".

Geller et al., J. Immunol., 146(10): 3280 (1991), "Generation of Lymphokine Activated Killer Activity in T Cells".

T.D. Geppert et al., J. Clin. Invest., 1988, 81, 1497, "Activation of T Lymphocytes by Immobilized Monoclonal Antibodies to CD3".

E.A. Grimm et al., J. Exp. Med., 1982, 155, 1823, "Lymphokine–Activated Killer Cells Phenomenon".

M. Izquierdo et al., Clin. Exp. Immunol., 1988, 74, 300, "Selection T cell subset depletion with anti–CD4 and anti–CD8 intact ricin immunotoxins".

C.M. Loeffler et al., Cancer Res., 51:2127 (1991), "Antitumor Effects of Interleukin 2 Liposomes and Anti–CD3–Stimulated T–Cells Against Murine MCA–38 Hepatic Metastasis".

E. Lotzova et al., Nat. Immun. Cell Growth Regul., 1987, 8, 219, "Augmentation of Antileukemia Lytic Activity by OKT3 Monoclonal Antibody: Synergism of OKT3 and Interleukin–2".

A.C. Ochoa et al., Cancer Res., 49: 963 (1989), "Lymphokine–activated Killer Activity in Long–Term Cultures with Anti–CD3 plus Interleukin 2: Identification and Isolation of Effector Subsets".

A.C. Ochoa et al., J. Immunol., 1987, 138, 2728, "Long–Term Growth of Lymphokine–Activated Killer (LAK) Cells: Role of Anti–CD3, $\beta$–IL 1, Interferon–$\gamma$ and –$\beta$".

L.E. Samelson et al., Proc. Natl. Acad. Sci. USA, 87: 4358 (1990), "Association of the fyn protein–tyrosine kinase with the T–cell antigen receptor".

R. Schwab et al., J. Immunol., 1985, 135, 1714, "Requirements for T–Cell Activation by OKT3 Monoclonal Antibody: Role of Modulation of T3 Molecules and Interleukin".

S. Shu et al., J. Immunol., 1985, 135, 2895, "Adoptive Immunotherapy of a Newly Induced Sarcoma: Immunlogic Characteristics of Effector Cells".

Smyth, J. Exp. Med, 171: 1269 (1990),"Interleukin 2 Induction of Pure–Forming Protein Gene Expression in Human Peripheral Blood CD8+T Cells".

(List continued on next page.)

Primary Examiner—Lila Feisee
Assistant Examiner—Phillip Gambel
Attorney, Agent, or Firm—Foley & Lardner

[57] ABSTRACT

The present invention provides a method for enhancing the immunotherapeutic activity, e.g., cytotoxicity, of immune cells by depleting immune cells of a cell subset that down-regulates the immune response, such as either CD4+ or CD8+ lymphocytes. The remaining depleted immune cells are then cultured in the presence of interleukin-2 (IL-2) and an antibody to a lymphocyte surface receptor, preferably an anti-CD3 monoclonal antibody (MoAb). The present invention also provides a method of enhancing the immunotherapeutic activity, e.g., cytotoxicity, of immune cells by culturing immune cells in the presence of IL-2 and an antibody to a lymphocyte surface receptor, preferably an anti-CD3 MoAb; separating a cell subset capable of developing immunotherapeutic activity, e.g., cytotoxicity, from the cultured immune cells, e.g., either CD4+ or CD8+ lymphocytes; and then subculturing the separated lymphocytes in the presence of IL-2.

5 Claims, 5 Drawing Sheets

OTHER PUBLICATIONS

Smyth, *J. Immunol.*, 148: 3289 (1991), "Regulation of Lymphokine–Activated Killer Activity and Pore–forming Protein Gene Expression in Huan Peripheral Blood $CD8^+T$ Lymphocytes".

C.–C. Ting et al., *Immunol. Invest.*, 1990, 19, 347, "Anti–CD3 Antibody–Induced Activated Killer Cells Subsets of Killer Cells that Mediate Fast or Slow Lytic Reactions".

M. C. Turco et al., *Blood*, 1989, 74, 1651, Proliferative Pathways in $CD1^-CD3^+CD4^+CD8^+$ T Prolymphocytic Leukemic Cells: Analysis with Monoclonal Antibodies and Cytokines.

R. J. van de Griend et al., *J. Immunol.*, 1987, 138, 1627, "Lysis of Tumor Cells by $CD3^+4^-8^-16^+$ T Cell Receptor $\alpha\beta$–Clones, Regulated Via CD3 and CD16 Activation Sites, Recombinant Interleukin 2, and Interferon $\beta$".

W. H. West et al., *J. Immunol.*, 1977, 118, 355, "Natural Cytotoxic Reactivity of Human Lymphocytes Against a Myeloid Cell Line: Characterization of Effector Cells".

Ochas et al., *FASEB Journal*, 3(3)A: 826 (abstract) (1989), "T Cels Can Develop High Lak Activity: Possible Regulatory Circuits".

Lotze et al., *Cancer Res.*, 41: 4420 (1981), "Lysis of Fresh and Cultured Autologous Tumor by Human Lymphocytes Cultured in T–Cell Growth Factor".

Balldegrun et al., *Cancer Res.*, 48: 206 (1988), "Interleukin 2 Expanded Tumor–infiltrating Lymphocytes in Human Renal Cell Cancer: Isolation, Characterization, and Antitumor Activity".

Maghazachi et al., *J. Immunol.*, 141: 4039 (1988), "Influence of T Cells on the Expression of Lymphokine–Activated Killer Cell Activity and In Vivo Tissue Distribution".

Damle et al., *J. Exp. Med.*, 158: 159 (1983), "Immunoregulatory T Cell Circuits in Man".

Lewis et al., *PNAS, USA*, 85: 9743 (1988), "Restricted production of interleukin 4 by activated human T cells".

Halvorsen et al., *Scand J. Immunol.* 27, 555–563, 1988, "Role of Accessory Cells in the Activation of Pure T Cells via the T Cell Receptor–CD3 Complex or with Phytohaemaggloutnin".

Halvorsen et al., *Scand J. Immunol.* 26, 197–205, 1987, "Activation of Resting, Pure $CD4^+$, and $CD8^+$ Cells via CD3".

Curti et al. J. Clin. Oncol. 11:652–660 (1993).

Whiteside et al. Cancer Immunol Immunother 39: 14–22 (1994).

Strome et al. J. Hematotherpy 2:63–73 (1993).

Michih Immunol Ser 61: 293–309 (1994).

Votze Cell Transplantation 2: 33–47 (1993).

Lindemann et al. Blut 59: 375–384 (1989).

Teichmann et al. Nat Immun 11: 117–132 (1992).

Ochos et al. Cancer Research 49: 963–968 (1989).

Bieva et al. Exp Hematol 17: 914–920 (1989).

Smyth, et al.; Journal of Experimental Medicine, vol. 171, pp. 1269–1281; Apr. 1990.

Ochoa, et al. "Long–Term Growth of Lymphokine–Activated Killer (LAK) Cell 59 Role of Anti–CD3, B–IL9, Interferon–$\gamma$ and –$\beta$" The Journal of Immunology, vol. 138, No. 8, pp. 2728–2733 1987.

Ochoa, et al. T Cells Can Develop High LAK Activity: Possible Regulatory Circuits FASEB Journal, vol. 3, No. 3 (Pt. 1), A826 (Abstract) 1989.

Geller, et al. Generation of Lymphokine–Activated Killer Activity in T Cells —Possible Regulatory Circuits The Journal of Immunology, vol. 146, No. 10, pp. 3280–3288 1991.

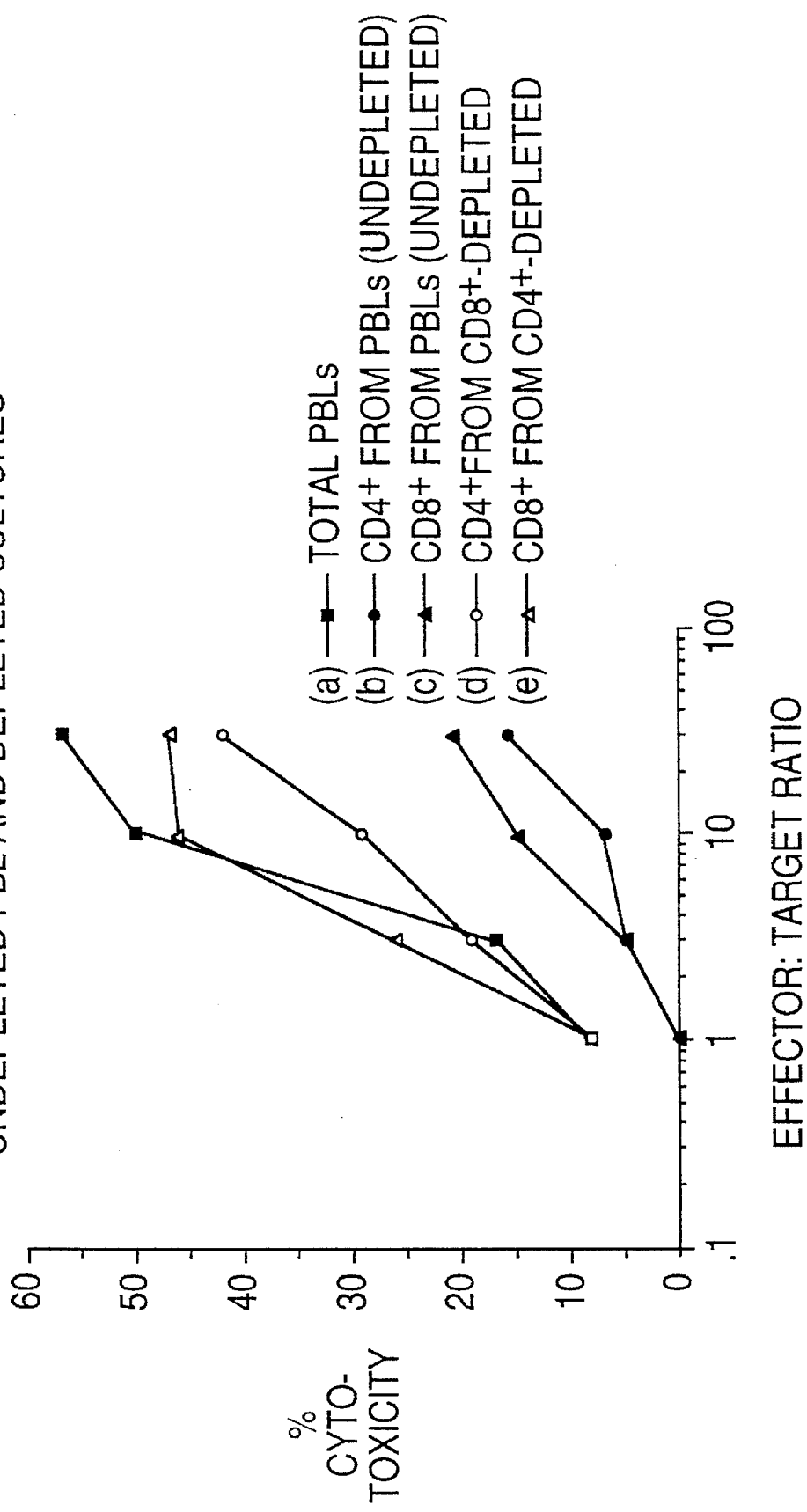

METHOD OF ENHANCING THE IMMUNOTHERAPEUTIC ACTIVITY OF IMMUNE CELLS BY DEPLETION OF CD8+ T CELLS

This application is a continuation of application Ser. No. 07/960,297, filed Oct. 13, 1992, now abandoned, which in turn is a continuation of application Ser. No. 07/681,074, filed Apr. 5, 1991, now abandoned.

FIELD OF THE INVENTION

This invention relates to the stimulation of the immunotherapeutic activity of immune cells. Specifically, this invention relates to the stimulation of antitumor activity upon the depletion or positive selection of specific cells or cell subsets of T lymphocytes.

BACKGROUND OF THE INVENTION

Peripheral blood mononuclear lymphocytes (PBLs) can be stimulated to develop lytic activity against fresh tumor cells, as well as several natural killer (NK) resistant targets, such as Daudi and HL60, after relatively short-term (3–5 days) culturing in the presence of recombinant interleukin-2 (IL-2). See, for example, M. Lotze et al., *Cancer Res.*, 41, 4420 (1981); C. Grimm et al., *J. Exp. Med.*, 155, 1823 (1982); and E. A. Grimm et al., "The Lymphokine-Activated Killer Cell Phenomenon: In Vitro and In Vivo Studies," in *Interleukins, Lymphokines and Cytokines*, S. Cohen and J. Oppenheim, eds., Academic Press, New York, p. 739 (1983). This function has been termed lymphokine activated killer (LAK) activity.

Initial reports suggested that precursors of cells with LAK activity did not express the T cell receptor as determined by anti-CD3 binding. See, E. A. Grimm et al., *J. Exp. Med.*, 157, 884 (1983). More recent reports have demonstrated that effector cells obtained from short-term culturing with IL-2 (2–5 days) are a $CD3^-$ population of cells that express the NK markers CD16 and/or CD56. The $CD3^+$ cells from such cultures have low lytic activity against NK-resistant targets. Thus, the $CD3^-$ population, with the NK markers CD16 and/or CD56, is responsible for the great majority of the LAK activity in PBL cultures. That is, $CD3^-$ cells appear to be the classical NK effector cells. See, for example, J. R. Ortaldo et al., *J. Exp. Med.*, 164, 1193 (1986); S. Ferrini et al., *J. Immunol.*, 138, 1297 (1987); K. Itoh et al., *J. Immunol.*, 136, 3910 (1986); and J. H. Phillips et al., *J. Exp. Med.*, 164, 814 (1986).

Reversible induction of NK activity in cloned cytotoxic lymphocytes in response to IL-2 and interferon (IFN) has been reported. See, C. G. Brooks, *Nature*, 305, 155 (1983). Furthermore, the generation of large numbers of cells with LAK activity using relatively long-term cultures (10–30 days) of PBLs stimulated with the anti-CD3 monoclonal antibody (MoAb) OKT3, in combination with IL-2 has been reported (CD3-LAK cells or T-AK cells). See, A. C. Ochoa et al., *J. Immunol.*, 138, 2728 (1987). The effector cells in these long-term IL-2 and OKT3 cultures include $CD3^-$ cells, as well as a $CD3^+$ population that is both CD4 and CD8 negative, and expresses the γδ chains of the T cell receptor. In contrast, the effector cells in short-term IL-2 and OKT3 cultures (2–5 days) are predominantly $CD3^-$ cells.

Numerous studies have shown that very little LAK activity appears to be mediated by the classically described $CD4^+$ or $CD8^+$ T cells. Furthermore, $CD4^+$ or $CD8^+$ cells isolated from cultures of mixed PBL populations, which are activated with an antibody to a lymphocyte surface receptor, such as the anti-CD3 monoclonal antibody OKT3, and continuously cultured with IL-2, do not develop significant levels of NK or LAK activity, as determined immediately upon their isolation from the total population. See, for example, A. C. Ochoa et al., *Cancer Res.*, 49, 963 (1989). For example, at an effector to target ratio of about 30:1, i.e., a ratio of the number of T cells capable of mediating cytotoxicity to the number of tumor cell line targets, the cytotoxicity of $CD4^+$ or $CD8^+$ subsets is no more than about 15–20%.

It has been noted that when PBLs are stimulated in mixed lymphocyte culture (MLC), the $CD4^+$ cells are minimally cytotoxic. Furthermore, when the $CD4^+$ population is stimulated in MLC in the absence of other T cells, they develop greater cytolytic activity. See, E. L. Reinherz et al., *Proc. Natl. Acad. Sci. USA*, 76, 4061 (1979). However, this cytotoxicity is antigen specific, and does not involve tumor killing activity.

It has also been recently shown that $CD8^+CD11b^+$ cells can develop LAK activity. In this specific situation, the $CD8^+$ T cells were isolated from the PBL population before the initiation of culture in the presence of IL-2 alone. However, this method did not involve anti-CD3 MoAb stimulation; however, this method did involve separating the T cells with sheep red blood cells, which in itself can produce a stimulating signal through the CD2 receptor. Thus, NK cells, which express the CD2 receptor, can also be activated. See, U. Dianzani et al., *Eur. J. Immunol.*, 19, 1037 (1989).

$CD4^+$ and $CD8^+$ cells cultured in the presence of IL-2 alone have been shown to express the lytic machinery, but LAK activity was not demonstrated nor was cell growth reported. See, M. J. Smyth et al., *J. Exp. Med.*, 171, 1269 (1990). Finally, it has been shown that tumor infiltrating lymphocytes (TILs), which appear to be effective in the treatment of solid tumors, are primarily $CD8^+$. See, for example, S. Shu et al., *J. Immunol.*, 139, 295 (1987); and A. Belldegrun et al., *Cancer Res.*, 48, 206 (1988).

The identification of cells that can mediate cytotoxicity, e.g., LAK activity, is important both for an understanding of the interactions of the immune system as well as for the potential development of effective methods of immunotherapy. One of the limitations of current LAK therapies for the treatment of tumors is that LAK cells appear to be transported via the reticuloendothelial system which, in some cases, limits the accessibility of LAK cells to certain tumors. See, for example, A. A. Maghazachi et al., *J. Immunol.*, 141, 4039 (1988). T cells, on the other hand, circulate through the lymphatic system and provide greater accessibility to most tumors.

While most NK and LAK activity in cultures stimulated with IL-2 alone or IL-2+anti-CD3 appears not to be mediated by $CD4^+$ or $CD8^+$ cells, what has been needed is to determine if these T cells, under the appropriate conditions, could develop high cytotoxicity, e.g., specific or nonspecific lytic activity. Thus, what is needed is a method for the stimulation of high cytotoxicity, preferably high nonspecific lytic, e.g. NK or LAK, activity in T cells, which can provide antitumor therapeutic efficacy.

SUMMARY OF THE INVENTION

A method has been developed to enhance the immunotherapeutic activity of immune cells by: separating at least one cell subset, or subpopulation, that is capable of down-regulating the immunotherapeutic activity, e.g., cytotoxicity, of an immune cell population, from that immune cell population to form a depleted immune cell population; and culturing the depleted immune cell population in the presence of IL-2 and an antibody to a lymphocyte surface receptor. Preferably, this method reduces or eliminates a regulatory mechanism from the immune cell population, which allows the remaining cells to more fully express their immune function. The immunotherapeutic activity of the remaining immune cell population, as represented by a measure of the cytotoxicity or antitumor activity of the cells, can be increased by a factor of at least about 1.2, preferably by a factor of at least about 2.0.

The depleted immune cell population is preferably cultured in a first medium in the presence of both IL-2 and an antibody to a lymphocyte surface receptor. More preferably, the cells are cultured in both IL-2 and an antibody to a lymphocyte surface receptor for only the first 48 hours. Thereafter, the culturing preferably occurs in the presence of IL-2 without any additional amount of the antibody to a lymphocyte surface receptor. Alternatively, the depleted immune cell population can be stimulated by an antibody to a lymphocyte surface receptor and thereafter cultured with IL-2; however, in certain situations culturing with IL-2 may not be necessary.

The immune cell population can include all immune cells that are part of an immune system, such as T cells, B cells, NK cells, and macrophages. Any of these cells, or a combination of these cells, can be depleted by the method of the present invention, with a resultant increased immunotherapeutic, e.g., antitumor, effect. As used herein, the "immune cell population" can be, and is preferably, a total, i.e., unseparated or undepleted population as obtained from a whole blood sample; however, the "immune cell population" can be any portion of a total population that contains a cell subset or subpopulation that down-regulates the immunotherapeutic activity of the larger population, or is capable of developing immunotherapeutic activity itself.

Preferably, this method involves the depletion of T lymphocyte populations, e.g., PBL populations, before the initiation of culture with IL-2 and an antibody to a lymphocyte surface receptor. More preferably, the separated cells are $CD4^+$ or $CD8^+$ lymphocytes, or more specific subsets of each of these populations. The cytotoxicity, or antitumor activity enhanced can be specific or nonspecific lytic activity. Preferably, it is nonspecific lytic, e.g., LAK, activity.

As a result of the removal or depletion of specific cell subsets that inhibit antitumor activity, the remaining immune cells preferably develop increased immunotherapeutic activity as represented by levels of cytotoxicity generally equivalent to that seen in NK populations in the same cultures. The cytotoxic activity of the cultured NK cells can in some situations also be increased above that of uncultured NK cells by the methods of the present invention. Thus, the remaining immune cell population preferably develops an increased immunotherapeutic activity as represented by an increase in the level of cytotoxicity, i.e., antitumor activity, by a factor of at least about 1.2, and more preferably by about 2.0.

To effectuate this enhanced immunotherapeutic activity, e.g., increased antitumor activity, the culturing process of the depleted immune cell populations preferably occurs over a period of at least about two days, and more preferably over a period of at least about ten days. According to specific preferred embodiments of the invention, the culturing process involves: stimulating the depleted immune cell population with an antibody to a lymphocyte surface receptor during the first 48 hours of culturing in a first medium that also contains IL-2; removing the depleted immune cell population from the first medium; and subculturing the depleted immune cell population in a second medium that contains IL-2 without any additional amount of an antibody to a lymphocyte surface receptor. The antibody to a lymphocyte surface receptor is preferably an anti-CD3 MoAb, i.e., an antibody against the antigen receptor complex CD3, such as OKT3.

Furthermore, a method has been developed to enhance the cytotoxicity of immune cells by first culturing an immune cell population to form a cultured immune cell population; separating, i.e., positively selecting, a cell subset, or subpopulation, that is capable of developing immunotherapeutic activity, e.g., cytotoxicity; and separately culturing, i.e., subculturing, the separated cells in a second medium in the presence of IL-2.

Preferably, by using this method and positively selecting a cell subpopulation, the immunotherapeutic activity, as represented by the cytotoxicity, of this subpopulation can be increased by a factor of at least about 1.2, preferably by a factor of at least about 2.0. Preferably, the separated cells are $CD4^+$ or $CD8^+$ lymphocytes, or subsets of each of these populations.

To effectuate this enhanced immunotherapeutic activity, e.g., increased antitumor activity, of immune cell subpopulations, the initial culturing process preferably involves the use of IL-2 and an antibody to a lymphocyte surface receptor to produce what is referred to as CD3-LAK cells or T-activated killer cells (T-AK). The initial culturing process of the unseparated or undepleted, i.e., total, immune cell populations preferably occurs over a period of at least about three days, and more preferably at least about five days. Alternatively, the initial culturing process can involve stimulation by an antibody to a lymphocyte surface receptor and thereafter cultured with IL-2; however, in certain situations culturing with IL-2 may not be necessary. The subsequent subculturing process in IL-2 of each cell subset preferably occurs over a period of at least about three days, and more preferably at least about ten days. These results are shown in FIGS. 1–5.

BRIEF DESCRIPTION OF THE DRAWINGS

FIG. 4 illustrates the LAK activity (% cytotoxicity) of: (a) an undepleted, i.e., unseparated or total, PBL population stimulated with the anti-CD3 MoAb OKT3 and continuously cultured with IL-2; (b) the $CD4^+$ cells isolated from the cultured undepleted PBLs; (c) the $CD8^+$ cells isolated from the cultured undepleted PBLs; (d) $CD4^+$ cells isolated from a cultured $CD8^+$-depleted PBL population; and (e) $CD8^+$ cells isolated from a cultured $CD4^+$-depleted PBL population.

DETAILED DESCRIPTION OF THE INVENTION

Figure 1:
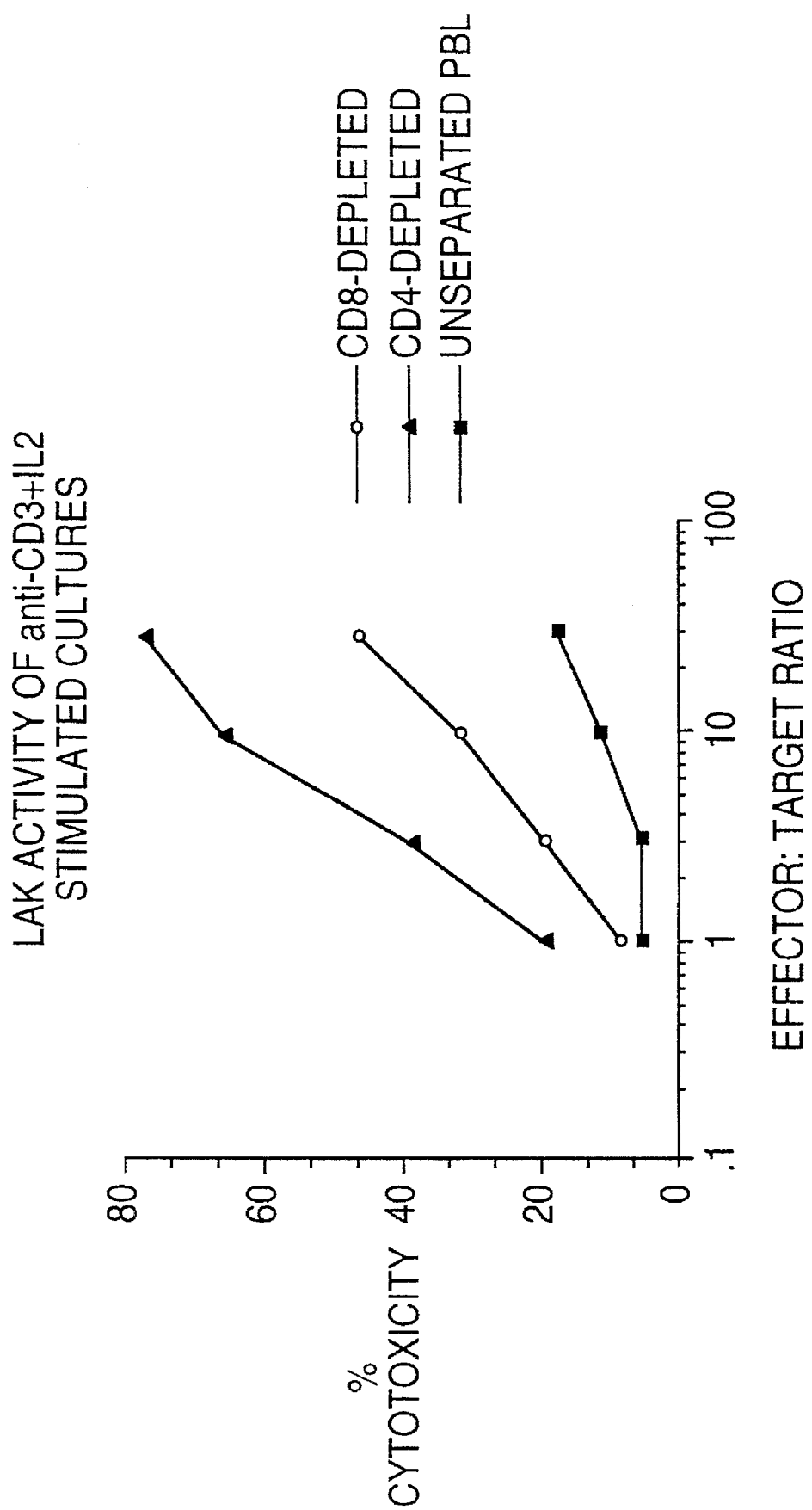
FIG. 1 illustrates the LAK activity (% cytotoxicity) of a $CD8^+$-depleted PBL population, $CD4^+$-depleted PBL population, and unseparated PBLs, stimulated with the anti-CD3 MoAb OKT3 and continuously cultured with IL-2.

As used herein, LAK activity is defined as the ability of lymphocytes to lyse tumor cells, and to a lesser degree normal cells. This activity in lymphocytes is typically stimulated by lymphokines, such as IL-2. In the examples herein, LAK activity refers to the ability to lyse the human NK-resistant tumor target, HL60. NK activity is defined as the ability to lyse tumor cells, but not normal cells, which does not result from prior stimulation. In the examples herein, NK activity refers to the ability to lyse the human tumor line K562. Since similar results were obtained with both tumor lines, only the LAK results with HL60 are shown.

As used herein, the "immune cell population" can be, and is preferably, a total, i.e., unseparated or undepleted population as obtained from a whole blood sample; however, the "immune cell population" can be any portion of a total population that contains a cell subset or subpopulation that down-regulates the immunotherapeutic activity of the larger population, or is capable of developing immunotherapeutic activity itself. The immune cell population can include all immune cells that are part of an immune system, such as T cells, B cells, NK cells, and macrophages. Any of these cells, or a combination of these cells, can be depleted by the method of the present invention, with a resultant increased immunotherapeutic, e.g., antitumor, effect.

As used herein, "depleted immune cell population" preferably refers to a total cell population derived from a sample of whole blood with at least one cell subset or subpopulation, which down-regulates the immunotherapeutic activity of the total population, removed therefrom. Alternatively, however, "depleted immune cell population" can be a subpopulation or subset itself, which upon further removal of a cell type can exhibit an enhanced immunotherapeutic activity.

As used herein, "culturing" indicates the process whereby cells are placed in a tissue culture medium comprising nutrients to sustain the life of the cells, and other additives, such as the growth factor IL-2. This process can take place in any vessel or apparatus. The process can involve various stages of culturing and subculturing. Typically, cells are initially cultured and expanded, i.e., increased in size and number. These expanded cells are then counted and divided into groups, or subcultures, for further culturing and expansion. The expanded cells from each of these subcultures are then divided into additional subcultures, for further culturing and expansion. Each of the culturing or subculturing steps typically lasts about 48 hours, with fresh tissue culture medium used in each culture.

As used herein "immunotherapeutic" refers to any of a variety of immune responses of immune cells. This includes a cytotoxic or antitumor effect. As used herein "cytotoxicity" and "antitumor activity" are used interchangeably and include specific lytic activity, and the nonspecific lytic activity of lymphokine activated killer (LAK) cells and natural killer (NK) cells. In general, the methods of the present invention are preferably directed to enhancing the cytotoxicity, i.e., antitumor activity, of immune cells, preferably T lymphocytes.

Depletion of Cell Subpopulations

The depletion of at least one cell subset, or subpopulation, such as CD4+, or CD8+ cells, or specific subsets of either of these cell populations, that is capable of down-regulating (i.e., preventing the effector cells from developing the immunotherapeutic, e.g., cytolytic, machinery) the immunotherapeutic activity of an immune cell population, from the total immune cell population results in the development of enhanced immunotherapeutic activity, as represented by increased cytotoxicity. Specifically, the depletion of a T lymphocyte subpopulation, that inhibits the antitumor activity of a total immune cell population, from the total immune cell population results in the development of high levels of LAK activity in the remaining "depleted" immune cells.

This effect occurs in response to culturing the depleted immune cell population in the presence of interleukin-2 (IL-2) and an antibody to a lymphocyte surface receptor. Preferably, this occurs in response to initial stimulation with an antibody to a lymphocyte surface receptor and continuous culturing, or subculturing, in the presence of IL-2. That is, preferably the cells are cultured in a first tissue culture medium with IL-2 and the lymphocyte surface receptor antibody. Thereafter, the cells are cultured, or subcultured, in a second tissue culture medium with IL-2 but without any additional amount of an antibody to a lymphocyte surface receptor. Further cultures, or subcultures, in the presence of IL-2 can also occur. Alternatively, the cells can be stimulated with an antibody to a lymphocyte surface receptor, and then optionally cultured with IL-2.

Although the lymphocyte surface receptor antibody is preferably not added to any of the subcultures after the first 48 hours, it can be present in each of the subsequent subcultures if the cultured cells from the first culture are not washed before the addition of a second tissue culture medium containing IL-2 without any surface receptor antibody. Any protocol, however, for culturing immune cells in which the immune cells are in the presence of both IL-2 and an antibody to a lymphocyte surface receptor at any time and for any period of time in the overall course of the culturing process is also within the scope of the present invention. Furthermore, any protocol in which the cells are stimulated with the antibody alone in the tissue culture media without any further IL-2 culturing is within the scope of the present invention.

In the present invention the cells are preferably cultured with IL-2 for at least about 2 days, more preferably for at least about ten days. Similar results have been obtained from cells cultured in the presence of IL-2 for as long as 30 days, with subculturing occurring approximately every 48 hours. As stated above, the cells are preferably stimulated with an antibody to a lymphocyte surface receptor during the first 48 hours of culture.

The antibody to a lymphocyte surface receptor can be any of a variety of monoclonal antibodies against a surface antigen receptor complex. Useable antibodies include an anti-CD2, anti-CD4, anti-CD5, anti-CD28, anti-CD11b, etc., monoclonal antibody (MoAb). The antibody used in the present invention is preferably an anti-CD3 monoclonal antibody. The antibodies can be used alone or in various combinations with other antibodies. For example, anti-CD3 can be used in combination with anti-CD2, anti-CD4, anti-CD5, anti-CD28, or anti-CD11b, for effective results. Anti-CD3 or anti-CD2 can each be used individually as the antibody in the cultures. The anti-CD3 MoAb can be, but is not limited to, OKT3, WT32, Leu-4, SPV-T 3c, RIV9, 64.1, etc. More preferably, the anti-CD3 MoAb is OKT3, which is available from Ortho, a division of Johnson & Johnson.

The interleukin-2 (IL-2) is a commercially available T cell growth factor. It can be a naturally occurring IL-2 or it can be recombinant IL-2. It is believed that other lymphokines can also be used in the present invention to provide the lymphokine activated cells. These include IL-1, IL-4, IL-6, interferons, etc. It is envisioned that they can be used alone, in sequence, or in combination with IL-2 in the culturing media.

The immune cells, preferably T lymphocytes, and more preferably peripheral blood mononuclear lymphocytes can be depleted of specific T cell subsets by any method. Preferably, the PBLs are depleted of specific subsets by negative depletion using magnetic beads. Typically, this involves the labelling of the PBLs with an antibody to a lymphocyte surface receptor for the T cells that are to be removed from the total PBL population. This mixture of labelled and unlabelled cells are then mixed with goat anti-mouse IgG-coated magnetic beads. A complex of the beads and the labelled T cells, i.e., those cells complexed with the surface receptor antibody, is formed. The beads/ labelled T cell complexes are then separated from the mixture using a magnetic separator. In this way, a specific T cell subset, or portion thereof, can be removed from the PBL mixture.

The specific immune cell subset removed can be any that down-regulates the immunotherapeutic activity, preferably the cytotoxic activity, of the total immune cell population. This can include: $CD4^+$, or any of its subsets such as 2H4 or 4B4; $CD8^+$, or any of its subsets; NK cells, or any of its subsets; macrophages; B cells; and the like. Preferably, the immune cell subsets removed are T cell subsets, and more preferably they are $CD4^+$ or $CD8^+$ cells.

In general, a typical sample of PBLs from a sample of human whole blood contains about 20–30% $CD8^+$ cells and about 30–50% $CD4^+$ cells. In order to increase the immunotherapeutic activity, e.g. antitumor activity, of an immune cell population according to the present invention, the cells that inhibit or down-regulate the immunotherapeutic activity of the population need only be removed until an increase in the immunotherapeutic activity, as represented by cytotoxicity, by a factor of about 1.2 is observed in the remaining cell population. Preferably, in order to increase the immunotherapeutic activity of immune cells according to the present invention, the number of $CD4^+$ or $CD8^+$ cells are reduced in the depleted immune cell populations by at least about 75%, more preferably by at least about 90%. Most preferably, however, a "substantially completely depleted" immune cell populations, e.g., PBL populations, contain less than about 5% of the cell subset removed. For example, a "substantially completely $CD4^+$-depleted immune cell population" contains less than about 5% $CD4^+$ cells. Thus, the method of the present invention includes separating preferably at least about 75%, and more preferably at least about 90% of the $CD4^+$ or $CD8^+$ cells from PBLs to increase the immunotherapeutic activity, e.g., antitumor activity, of the remaining "depleted" cell population.

The increased immunotherapeutic activity of the immune cell populations is determined in vitro by the percent cytotoxicity, which is a measure of the ability of immune cells to destroy a radioactively labeled tumor target. That is, the antitumor activity is determined by a comparison of the level of radioactivity released in tissue culture media from the effector/target combination to the level of radioactivity in the culture media released from the target alone. Thus, increased immunotherapeutic activity, as defined herein, of immune cells is typically demonstrated by an increase in the percent cytotoxicity of the effector cells on human tumor cells. The human tumor cell lines can be any of a variety of cell lines commercially available, including leukemia cells and fresh tumor targets. Preferably, they are leukemia cells.

According to specific embodiments of the present invention, increased antitumor activity is demonstrated by an increase in the percent cytotoxicity level by a factor of at least about 1.2. Preferably, antitumor activity is demonstrated by an increase in the percent cytotoxicity by a factor of at least about 2.0.

As can be seen from FIG. 1, the amount of cytolytic activity of either the $CD4^+$-depleted or the $CD8^+$-depleted cultures is greater than that of unseparated, i.e., total or undepleted, PBLs regardless of the effector to target ratio. The LAK activity was measured at several time points between 10 and 30 days of culture, with similar results regardless of the day of assay. Similar results are obtained with $CD4^+$-depleted and $CD8^+$-depleted populations in short-term, i.e., about three to five day, cultures. It is envisioned that shorter time periods for culturing will produce similar results.

These observations could be explained in several manners. For example, the enhanced LAK activity could be the result of a relative enrichment in $CD3^-CD16^+$ and/or $CD56^+$ NK cells, or $CD3^+CD4^-CD8^-$ ($\gamma\delta$) T cells, both of which have been previously shown to mediate LAK activity. It has been determined, however, that the enhanced LAK, as well as NK activity, is preferably the result of the activation of the cell subpopulations, i.e., $CD4^+$ or $CD8^+$ T cells, that remain in the depleted cultures.

This was determined by labelling the cells from the depleted PBL populations with anti-CD8 MoAb (in the $CD4^+$-depleted cultures) or anti-CD4 MoAb (in the $CD8^+$-depleted cultures), and positively sorting them using a fluorescence-activated cell sorter (FACS). When cells from $CD4^+$-depleted cultures are separated into $CD8^+$ and $CD4^-CD8^-$ populations, and tested for LAK and NK activity immediately after sorting, both $CD8^+$ cells and $CD4^-CD8^-$ cells mediate significant levels of LAK and NK activity.

Figure 2:
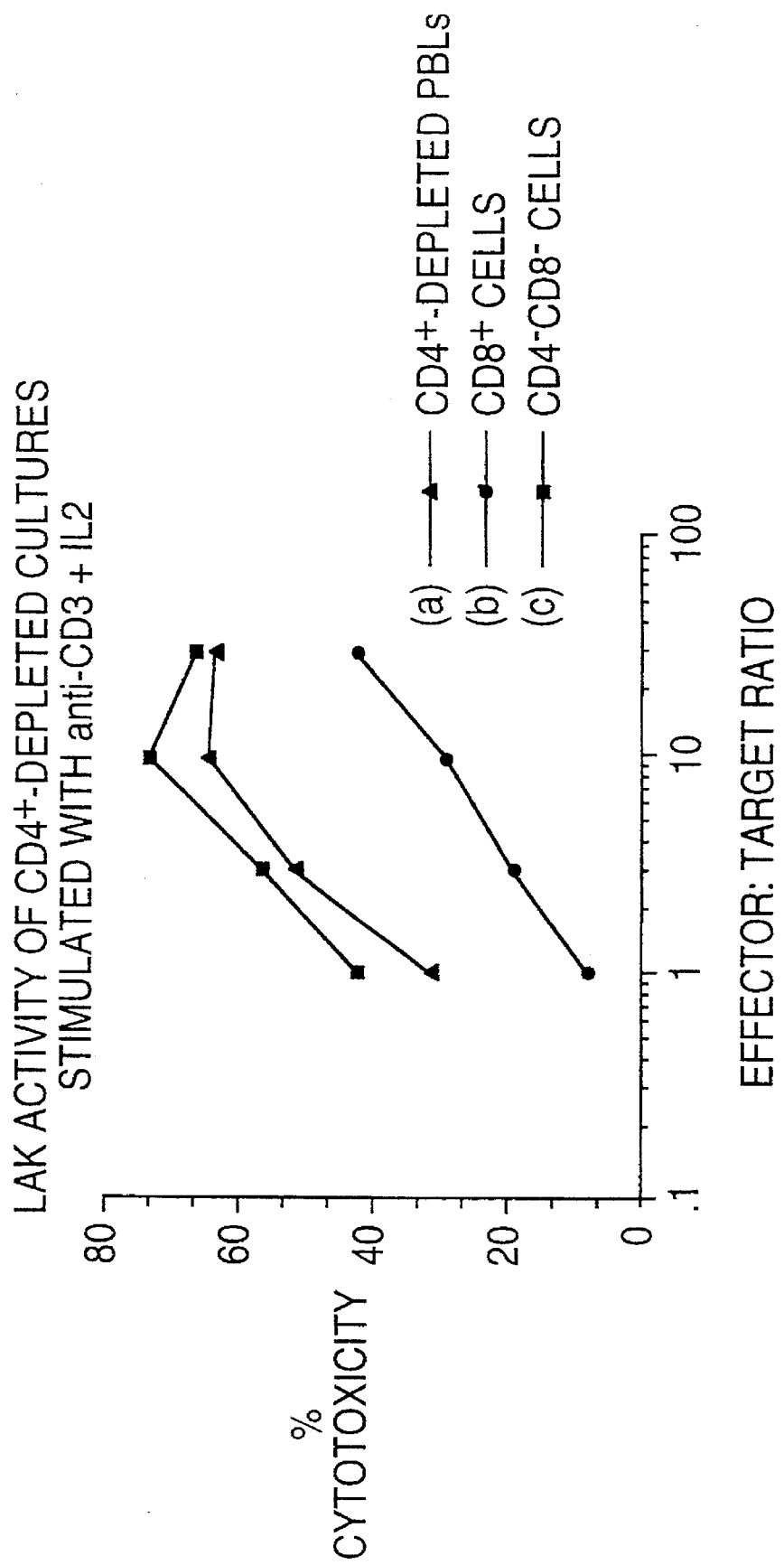
FIG. 2 illustrates the LAK activity (% cytotoxicity) of: (a) a $CD4^+$-depleted PBL population stimulated with the anti-CD3 MoAb OKT3 and continuously cultured with IL-2; (b) the $CD8^+$ cells isolated from the cultured $CD4^+$-depleted PBLs; and (c) the remaining $CD4^-CD8^-$ cell population isolated from the cultured $CD4^+$-depleted PBLs.
Figure 3:
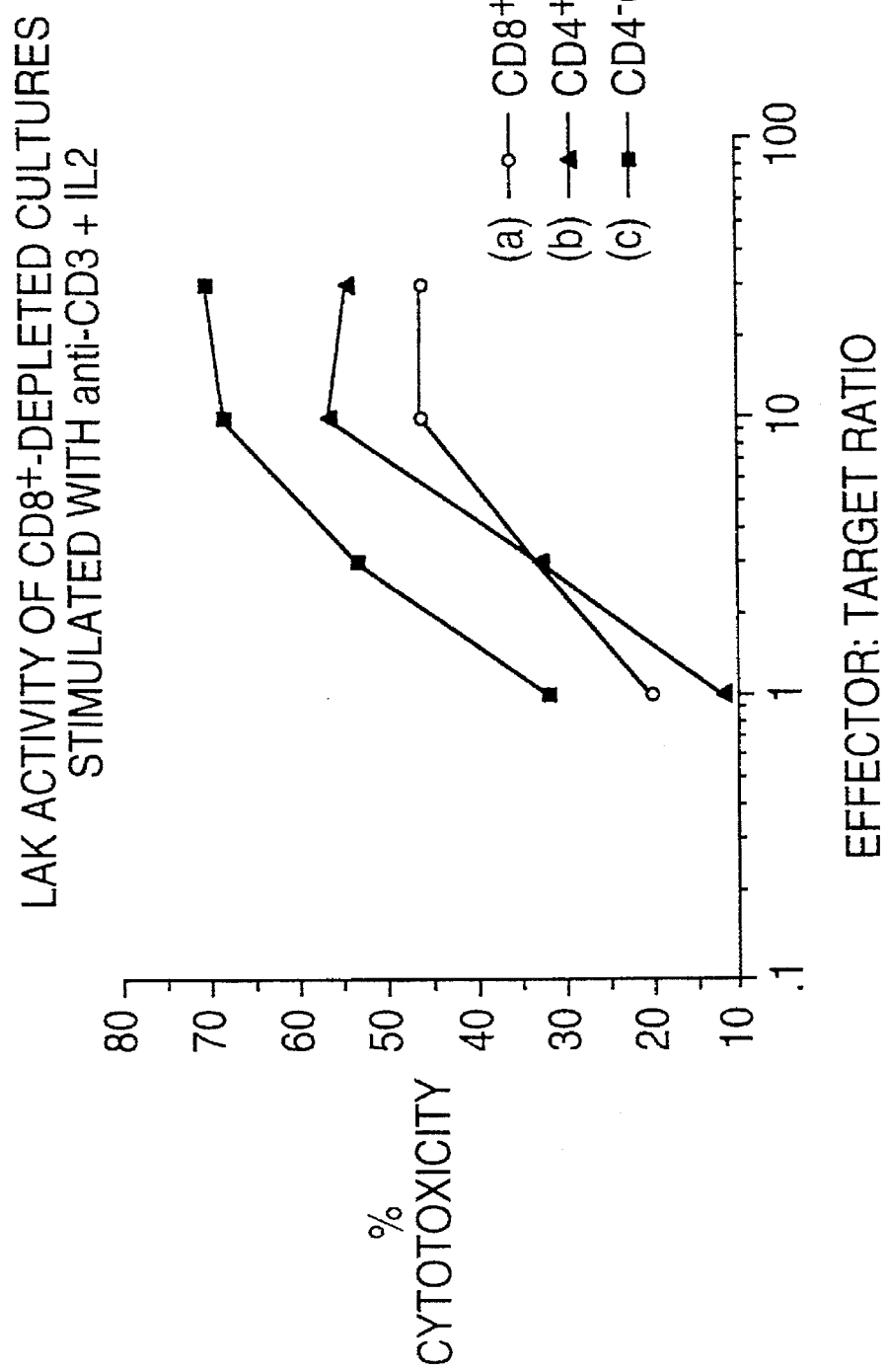
FIG. 3 illustrates the LAK activity (% cytotoxicity) of: (a) a $CD8^+$-depleted PBL population stimulated with the anti-CD3 MoAb OKT3 and continuously cultured with IL-2; (b) the $CD4^+$ cells isolated from the cultured $CD8^+$-depleted PBLs; and (c) the remaining $CD4^-CD8^-$ cell population isolated from the cultured $CD8^+$-depleted PBLs.

As shown in FIG. 2, the $CD4^-CD8^-$ cells demonstrate about 65% cytotoxicity at an effector to target ratio of about 30:1. The $CD8^+$ cells demonstrate about 40% cytotoxicity at an effector to target ratio of about 30:1. Similar results are observed when $CD8^+$-depleted populations are labelled with anti-CD4 MoAb and sorted into $CD4^+$ and $CD4^-CD8^-$ populations (FIG. 3). Additional phenotyping of the $CD4^-CD8^-$ cells in both types of cultures show them to be primarily $CD16^+Leu19^+$ or $CD3^+CD4^-CD8^-$.

In comparison, however, when cultured with IL-2 and an antibody to a lymphocyte surface receptor in an undepleted population of PBLs, isolated $CD4^+$ or $CD8^+$ cells do not develop such significant levels of NK or LAK activity. As can be seen by the results shown in FIG. 4, at an effector to target ratio of about 10:1, the cytotoxicity of $CD4^+$ or $CD8^+$ cell subsets is no more than about 10–15%, and at an effector to target ratio of about 30:1, the cytotoxicity of $CD4^+$ or $CD8^+$ cell subsets is no more than about 15–20%.

Results similar to those shown in FIG. 4 were obtained at various times between 10 and 30 days of culturing undepleted PBLs with IL-2 and the anti-CD3 MoAb OKT3. The $CD4^+$ and $CD8^+$ cells were isolated by negative depletion, however it is also possible to isolate them by positive FACS selection. Control cultures of CD4⁺-depleted or CD8⁺-depleted cells were sorted to obtain CD8⁺ and CD4⁺ cells, respectively. As shown in FIG. 4, CD8⁺ and CD4⁺ cells from the depleted cultures developed significant levels of LAK activity, i.e., at least about 40% cytotoxic activity at an effector to target ratio of about 30:1. Thus, although CD4⁺ and CD8⁺ cells do not show significant LAK or NK activity when tested immediately after isolation from CD3-LAK cultures, CD4⁺ and CD8⁺ cells can develop high LAK activity if one of these subsets is depleted from the PBL population prior to the initiation of culture.

Although not intending to be limiting in any manner, these results suggest that the development of LAK activity by T cells subpopulations is inhibited in the PBL cultures. It is believed that this inhibitory effect is the result of T cells, and possibly other immune cells, such as macrophages or B cells, that prevent the development of LAK activity by the other T cell subsets. Furthermore, it is believed that the inhibitory T cells generally exert their effect only if present throughout the entire culture period.

Positive Selection of Cell Subsets

Cell subpopulations, such as CD4⁺ or CD8⁺ cells, or specific cell subsets of these populations, separated from CD3-LAK cells, i.e., T-AK cells, show negligible LAK activity. These T-AK cells are typically cultured in the presence of IL-2 and an antibody to a lymphocyte surface receptor for about five days. It has been determined, however, that if the CD4⁺ and CD8⁺ cells are subsequently cultured separately in the presence of IL-2 alone, each individual population rapidly develops LAK activity.

The initial culturing process of the undepleted PBL populations preferably occurs over a period of at least about three days, and more preferably at least about five days. The subsequent culturing process in IL-2 of each cell subset preferably occurs over a period of at least about three days, and more preferably at least about ten days. The subsequent culturing process can be carried out for up to about 30 days.

The subsequent culture of the separate CD4⁺ and CD8⁺ cell populations is done in the presence of preferably about 10–1000 units/ml IL-2, more preferably about 100–1000 units/ml IL-2. Upon being tested for LAK activity at various times throughout the culturing process of the separate cell subsets, both populations rapidly develop and maintain high levels of NK and LAK activity.

Specific immune cells, preferably T lymphocytes, can be separated from an unseparated, i.e., total population of immune cells, preferably PBLs by any method. Preferably, the specific cell subpopulations are separated from the total populations by positive selection using fluorescence-labelled monoclonal antibodies. Typically, this involves adding a fluorescein isothiocyanate-conjugated MoAb or a phycoerythrin-conjugated MoAb to a cultured immune cell population, incubating the cells with the conjugate for 30 minutes at 4° C., washing the cells, and sorting or selecting out the labelled cells using a fluorescence-activated cell sorter. For positively selecting CD8⁺ cells the monoclonal antibody OKT8 can be used, and for positively selecting CD4⁺ cells the monoclonal antibody OKT4 can be used, both of which are available from the Ortho Division of Johnson & Johnson.

Figure 5A:
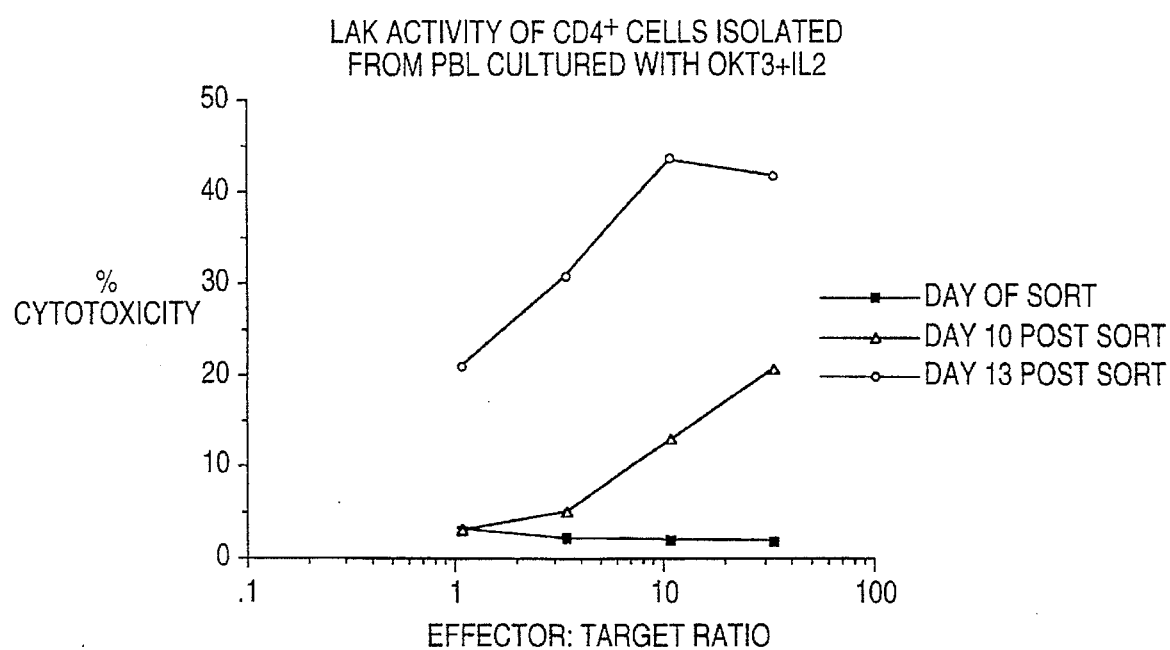
FIGS. 5A and 5B illustrate the LAK activity (% cytotoxicity) of CD4+ and CD8+ cells, respectively, isolated from cultured (OKT3 +IL-2) undepleted PBL populations and subsequently cultured with IL-2 alone. This data was obtained after five days of culturing the undepleted PBLs, i.e., "day of sort," and after ten and thirteen days of culturing each cell subset in IL-2.
Figure 5B:
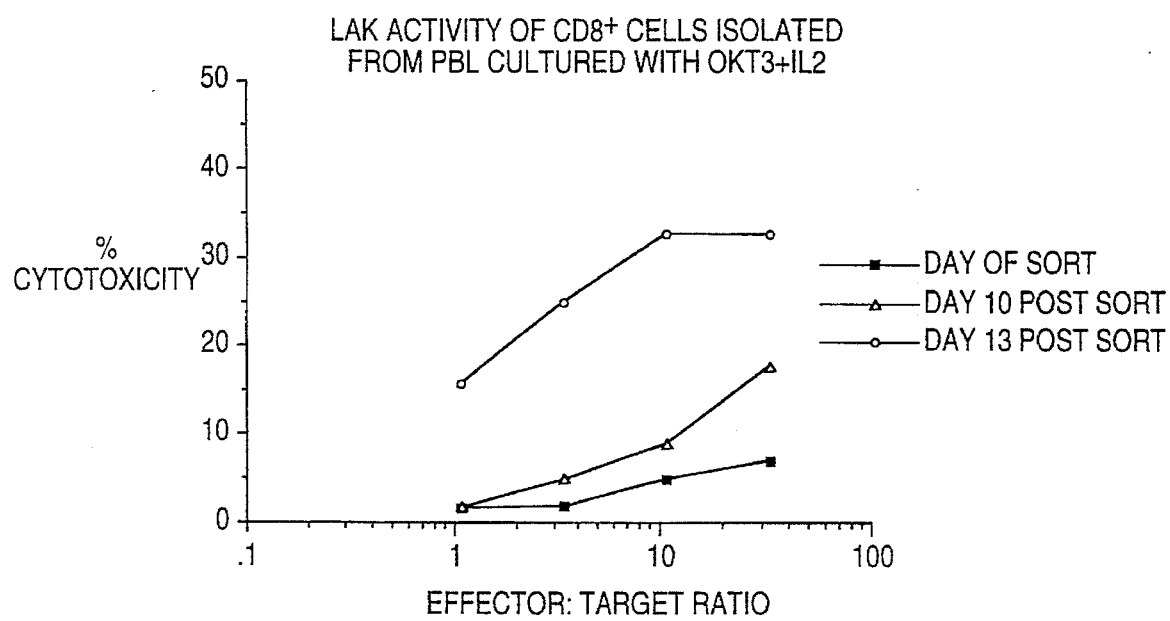

As can be seen in FIG. 5, both the CD4⁺ and CD8⁺ cell subsets show enhanced antitumor activity after ten days of culturing in IL-2. Although not shown, enhanced antitumor activity is seen after only three days of culturing in IL-2. Thus, using this methodology both CD4⁺ and CD8⁺ T cells can develop high levels of LAK activity.

Although this is in no way limiting, the results of the depletion and positive selection experiments suggest that the inhibition involves some ongoing regulatory interaction between CD4⁺ and CD8⁺ cells that is effectively abolished once they are separated, and that it is not due to an event in the initial activation process. That is, the observation that either CD4⁺ or CD8⁺ T cells can rapidly acquire LAK activity once isolated from PBL cultures suggests that the absence of expression of LAK activity by these cells in the unseparated populations is not the result of an irreversible process. Rather, the inhibition requires the continued interactions by the reciprocal T cell subsets. Mixing experiments designed to test this hypothesis demonstrate that the maintenance of a suppressor effect requires the continued interaction of viable metabolically active T cell subsets.

The inhibition could be mediated through direct cell contact or via soluble factors. Regulatory networks have been described in which both T cell subsets must be present in order to obtain suppression of function [N. K. Damle et al., *J. Exp. Med.*, 158, 159 (1983)]. These data suggest that there are inhibitory signals which prevent the development of LAK activity by CD4⁺ or CD8⁺ T cells in unseparated, i.e., total or undepleted, PBL populations. That is, there is a negative regulation of T cell function in PBL populations that appear to be mediated by the T cells themselves.

There are several soluble factors which might be involved in regulating the development of LAK activity by T cells, including interleukin-4 (IL-4) and transforming growth factor-$\beta$ (TGF-$\beta$). It is, of course, not necessary that both T cell subsets are regulated by the same factor.

IL-4 has been shown to inhibit both the growth and development of effector functions by LAK cells, although those effects appear to be principally on NK cells rather than T cells. See, for example, M. B. Widmer et al., *J. Exp. Med.*, 166, 1477 (1987); H. Spits et al., *J. Immunol.*, 141, 29 (1988); A. Nagler et al., *J. Immunol.*, 141, 2349 (1988); Y. Kawakami et al., *J. Exp. Med.*, 168, 2183 (1988). IL-4 is made primarily by CD4⁺ T cells, which suggest that it could play a role in regulating the development of LAK activity in CD8⁺ cells; however, this is not intended to be limiting in any way. See D. B. Lewis et al., *Proc. Natl. Acad. Sci. USA*, 85, 9743 (1988).

TGF-$\beta$ also has been shown to inhibit both NK and LAK activity. See, for example, A. Kasid et al., *J. Immunol.*, 141, 690 (1988); and J. J. Mule et al., *Cancer Immunol. Immunother.*, 26, 95 (1988). Furthermore, this inhibition has, in some cases, been shown to be based on the balance between the levels of IL-2 and TGF-$\beta$. See, for example, J. H. Kehrl et al., *J. Exp. Med.*, 163, 1037 (1986).

The addition of human TGF-$\beta_1$ (TGF-$\beta$), which is available from R & D Systems, Minneapolis, Minn., to either CD4⁺-depleted or CD8⁺-depleted populations upon the initiation of the culturing process results in the inhibition of the lytic function of the depleted populations. Specifically, the addition of TGF-$\beta$ in concentrations ranging from 0.1–30 ng/ml upon initiating the culture, and during each of the subculturing steps, demonstrates a dose-dependent decrease in the lytic activity, i.e., LAK activity, of the T cells. This effect is reversible upon the removal of TGF-$\beta$ from the culture medium.

TGF-$\beta$ is produced by both CD4⁺ and CD8⁺ cells under certain culture conditions. Given that both T cell subsets produce TGF-$\beta$, it is possible that it is only when both CD4⁺ and CD8⁺ cells are present that the level of TGF-$\beta$ produced reaches the point were it has an inhibitory effect in the presence of high levels of IL-2. After depletion of either T cell subset, the levels of TGF-β would be too low to have an inhibitory effect on the T cells; however, this is not intended to be limiting in any way.

The observations that either CD4⁺ or CD8⁺ cells can, under the appropriate conditions, develop LAK activity and that the generation of that LAK activity is regulated by the presence of the reciprocal T cell subset, have implications for protocols for adoptive immunotherapy. For example, under certain conditions it is preferable to have LAK activity mediated by T cells. Thus, the present invention opens the possibility of including T cells with LAK activity in future clinical trials. Such cells could possibly achieve complementary or different antitumor effects than have been observed in conventional protocols.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Isolation and Culture of Cells with LAK Activity

Peripheral blood lymphocytes (PBLs) were isolated from heparinized venous blood (human whole blood) by centrifugation over Ficoll-Hypaque according to the method of A. Boyum, *Scand. J. of Clin. Lab. Invest.*, 99, 77 (1968), which is incorporated herein by reference. Isolated mononuclear cells were washed three times with phosphate buffered saline (PBS, pH 7.4) (GIBCO Laboratories, Grand Island, N.Y.) and counted. CD4⁺ and CD8⁺ enriched cultures were obtained by negative depletion using magnetic beads (obtained from Baxter Healthcare Corporation, Deerfield, Ill.; also available from Advanced Magnetics, Massachusetts; or Dynal Corp., Norway). Briefly, PBLs were labelled by incubation with either of the monoclonal antibodies OKT4 or OKT8 (Ortho, Raritan, N.J.) for 30 minutes on ice. The cells were then washed twice with cold PBS and mixed with goat anti-mouse IgG-coated magnetic beads (obtained from Baxter Healthcare; also available from Dynal Corp., Norway) at a bead:cell ratio of 10:1. The bead/cell mixture was incubated for 30 minutes at 4° C. while rotating at 5–6 rpm. At the end of the incubation, the bead/cell suspension was diluted two-fold with cold PBS. Using a magnetic separator (Baxter Healthcare Corporation, Deerfield, Ill.), the beads were allowed to collect against the side of the test tube for five minutes. The supernatant containing unbound cells was then collected and transferred to a new tube. This process was repeated three times to completely remove the beads and bead-bound cells. The cells that remained in suspension (CD4⁺-depleted or CD8⁺-depleted PBLs) were washed and counted. This resulted in depleted PBL populations with less than about 5% contamination by the T cell subset removed. The cells remained essentially unchanged during subsequent culture.

Peripheral blood lymphocytes or depleted populations ($5 \times 10^6$ cells) were cultured in 25 cm² flasks (Corning, Corning, N.Y.) in 10 ml tissue culture medium (TCM). The TCM consisted of Rosewell Park Memorial Institute (RPMI) 1640 medium (available from GIBCO, Grand Island, N.Y.) supplemented with 25 mM Hepes [N-(2-hydroxyethyl) piperazine-N'-(2-ethanesulfonic acid)], 2 mM L-glutamine, 100 units/ml penicillin, 100 μg/ml streptomycin (penicillin/ streptomycin mix available from GIBCO, Grand Island, N.Y.), and 5% pooled heat-inactivated human serum. The cultures were supplemented with 1000 units/ml of highly purified recombinant human IL-2 from *E. coli* (Hoffman-LaRoche, Nutley, N.J.). [See, A. Wang et al., *Science*, 224, 1431 (1984); and S. A. Rosenberg et al., *Science*, 223, 1412 (1984), which are incorporated herein by reference]. The cultures were supplemented with 10 ng/ml of the anti-CD3 MoAb OKT3 (Ortho Division, Johnson & Johnson, Raritan, N.J.). The OKT3 was present in the culture during the first 48 hours. Thereafter, the OKT3 was diluted due to the addition of fresh TCM and IL-2. No additional OKT3 was added during the culturing process. Cultures were incubated at 37° C. in a humidified atmosphere of 5% $CO_2$. After the first 48 hours of culture, the cells were counted and subcultured at $0.5 \times 10^6$ cells/ml in TCM containing IL-2. Subsequently, the cells were counted and subcultured every 48 hours in fresh TCM with IL-2 at a concentration of $0.5 \times 10^6$ cells/ml.

EXAMPLE 2

Cell Sorting by Immunofluorescence

PBLs, CD4⁺-depleted PBLs, or CD8⁺-depleted PBLs were each cultured in OKT3+IL-2 as described above. At various times during the culture period, the cells were sorted on a fluorescence-activated cell sorter (FACS). PBL populations were labelled with fluorescein isothiocyanate- (FITC) conjugated or phycoerythrin- (PE) conjugated MoAb: OKT4 and OKT8 (Ortho). CD4⁺-depleted populations were labelled with OKT8, and CD8⁺-depleted populations were labelled with OKT4. The cells were incubated for 30 minutes at 4° C. and were then washed twice with cold PBS containing 2% fetal bovine serum. Cells were sorted on a FACS IV (Becton Dickinson, Mountain View, Calif.). Sorted cells were centrifuged and an aliquot restained to test the purity of the populations. All of the positively sorted populations used for determining LAK activity were more than 97% positive for the desired surface marker.

EXAMPLE 3

Cell-Mediated Lympholysis (CML)

CML assays were done as described in S.-L. Wee et al., *Hum. Immunol.*, 3, 45 (1981), which is incorporated herein by reference. Human tumor lines K562 (chronic myelogenous leukemia, obtained from American Tissue Type Culture Collection (ATTCC)) and HL60 (promyelocytic leukemia, ATTCC) were maintained in culture in RPMI 1640 with 10% fetal bovine serum (GIBCO, Grand Island, N.Y.). Cells were subcultured at $0.5 \times 10^6$/ml in fresh medium twice a week.

Cells of the line HL60 were not lysed by unstimulated PBLs and were therefore considered NK-resistant. LAK activity was measured as cytolytic against the NK-resistant targets HL60. NK activity was measured as cytolytic activity against the K562 targets.

Tumor cell line targets were labelled with 250–750 μCi of Na⁵¹CrO₄ (5000 μCi/ml, New England Nuclear, Boston, Mass.) for one hour at 37° C. These cells were washed three times in TCM, resuspended in culture media that did not contain IL-2, counted, and aliquoted at 500 targets/well in a 96-well V bottom plate (Costar, Cambridge, Mass.) into which the effector cells, i.e., the peripheral blood lymphocytes or depleted populations cultured as described above in Example 1, had been previously aliquoted at set concentrations. The effector:target cell ratios ranged from 30:1 to 1:1.

Plates were centrifuged at 65 g for five minutes and incubated in 5% $CO_2$ at 37° C. for four hours, after which 100 µl of media was harvested from each well into a scintillation vial with 2.5 ml of scintillation fluid (Biofluor, New England Nuclear, Boston, Mass.). Radioactivity was counted on a liquid scintillation counter (LKB, Turku, Finland).

Percent cytotoxicity was determined by the following equation (cpm=counts per minute):

$$\frac{\text{(experimental mean cpm)} - \text{(spontaneous release mean cpm)}}{\text{(maximal release mean cpm)} - \text{(spontaneous release mean cpm)}} \times 100$$

wherein "spontaneous release mean" is defined as the amount of $^{51}Cr$ released from target cells alone (background); "maximal release" is the total $^{51}Cr$ in the targets following lysis with a detergent such as Triton X-100; and "experiment mean" is the $^{51}Cr$ released in wells with targets and effectors.

Representative samples of the results of all experiments are displayed in FIGS. 1–5. Each data point in each figure represents an analysis of three separate samples analyzed after the same period of culture, i.e., between 10 and 30 days, and the same period of contact between the effectors and targets, i.e., about four hours.

EXAMPLE 4

Immunophenotyping

Cells ($1 \times 10^6$) were washed 3 times with HBSS after which they were incubated at 4° C. with 20 µl of the corresponding monoclonal antibody (OKT4 or OKT8 from Ortho, Rareton, N.J.). They were again washed 3 times with cold Hanks Balanced Saline Solution (HBSS) including 2% fetal calf serum and resuspended in 0.2% paraformaldehyde. Two color fluorescence measurements were performed on a Coulter Profile (Coulter Cytometry, Hialeah, Fla.) or a FACS IV (Becton Dickinson, Mountain View, Calif.).

EXAMPLE 5

Mixing Experiments $CD4^+$ or $CD8^+$ cells isolated from unseparated PBL T-AK cultures on day 5 were added at a 1:1 ratio into $CD4^+$-depleted, or $CD8^+$-depleted, populations, respectively, on day 0 of autologous cultures. Some of the cultures received irradiated cells. Lytic function was tested 4 days later as % cytotoxicity. The results as shown below in Table 1 demonstrated that the addition of nonviable irradiated cells did not prevent the development of lytic activity. However, the addition of non-irradiated, i.e., metabolically active, $CD4^+$ or $CD8^+$ cells completely suppressed the development of LAK activity by the $CD4^+$-depleted or $CD8^+$-depleted populations, respectively.

TABLE 1

$CD4^+$ and $CD8^+$ Cells From PBL Cultures Inhibits the Development of Lytic Function by $CD4^+$-Depleted and $CD8^+$-Depleted Cultures[a]

| | % Cytotoxicity | | |
|---|---|---|---|
| | 30:1 | 10:1 | 3:1 |
| $CD4^+$-Depleted | 38 | 26 | 15 |
| $CD4^+$-Depleted + $CD4^+$ from PBL | −4 | −1 | 1 |
| $CD4^+$-Depleted + irrad. $CD4^{+b}$ | 42 | 26 | 11 |
| $CD8^+$-Depleted | 25 | 14 | 9 |
| $CD8^+$-Depleted + $CD8^+$ from PBL | −1 | 2 | −4 |
| $CD8^+$-Depleted + irrad. $CD8^{+b}$ | 46 | 30 | 15 |

[a]$CD4^+$ and $CD8^+$ cells were positively sorted out of PBL stimulated with OKT3 + IL-2 and cultured for 5 days. The cells were added at a 1:1 ratio to autologous cultures which had been depleted of $CD4^+$ or $CD8^+$ cells, respectively. Lytic function was assayed on cell line HL60.
[b]Isolated $CD4^+$ and $CD8^+$ cells received 2500 rads.

The invention has been described with reference to various specific and preferred embodiments and techniques. However, it should be understood that many variations and modifications may be made while remaining within the spirit and scope of the invention. The relevant portions of the references cited herein are incorporated by reference.

What is claimed is:

1. A method of enhancing the immunotherapeutic activity of immune cells comprising:

(a) separating $CD8^+$ lymphocytes from a T cell population to form a $CD8^+$-depleted T cell population; and (b) culturing the $CD8^+$-depleted T cell population in the presence of an anti-CD3 antibody, during a first 48 hour time period of culture to provide a stimulated depleted T cell population; and (c) optionally culturing said stimulated $CD8^+$-depleted T cell population with IL-2, wherein said stimulated $CD8^+$-depleted T cell population exhibits increased antitumor activity when stimulated with IL-2, due primarily to the enhanced responsiveness to IL-2 of the CD4+ subpopulation thereof, when compared to a similarly treated undepleted T cell population.

2. The method of claim 1, wherein the step of separating $CD8^+$ cells from the T cell population comprises the steps of:

(a) labelling the T cell population with an antibody to a lymphocyte surface receptor for the $CD8^+$ cells;

(b) mixing the labeled T cell population with IgG-coated magnetic beads to form a complex of said beads and labeled $CD8^+$ cells; and (c) separating the complex from the mixture.

3. The method of claim 1, wherein said $CD8^+$-depleted T cell population contains less than 25% of the $CD8^+$ cells from the T cell population.

4. The method of claim 3, wherein said $CD8^+$-depleted T cell population contains less than 10% of the $CD8^+$ cells from the T cell population.

5. The method of claim 3, wherein said $CD8^+$-depleted T cell population contains less than about 5% of the $CD8^+$ cells from the T cell population.

* * * * *